(12) United States Patent
Sohn et al.

(10) Patent No.: US 8,286,492 B2
(45) Date of Patent: Oct. 16, 2012

(54) MODE DECOMPOSITION OF SOUND WAVES USING AMPLITUDE MATCHING

(75) Inventors: Hoon Sohn, Daejeon (KR); Chulmin Yeum, Daejeon (KR); Jeong-Beom Ihn, Bellevue, WA (US)

(73) Assignee: The Boeing Company, Chicago, IL (US)

( * ) Notice: Subject to any disclaimer, the term of this patent is extended or adjusted under 35 U.S.C. 154(b) by 368 days.

(21) Appl. No.: 12/634,284

(22) Filed: Dec. 9, 2009

(65) Prior Publication Data

US 2011/0132090 A1     Jun. 9, 2011

(51) Int. Cl.
*G01N 29/36* (2006.01)
(52) U.S. Cl. ............................. 73/628; 73/602
(58) Field of Classification Search ............ 73/597, 73/599, 600, 602, 628; 702/35, 36, 182, 702/183; 310/354, 365
See application file for complete search history.

(56) References Cited

U.S. PATENT DOCUMENTS

| | | | | |
|---|---|---|---|---|
| 5,381,385 | A * | 1/1995 | Greenstein ..................... | 367/140 |
| 6,006,163 | A * | 12/1999 | Lichtenwalner et al. ....... | 702/36 |
| 6,996,480 | B2 * | 2/2006 | Giurgiutiu et al. .............. | 702/35 |
| 7,151,465 | B2 * | 12/2006 | Barbot et al. ............. | 340/854.6 |
| 7,199,509 | B2 * | 4/2007 | Kuniyasu et al. ............. | 310/365 |
| 7,487,059 | B2 * | 2/2009 | Davis et al. .................... | 702/116 |
| 7,552,027 | B2 | 6/2009 | Kearns et al. | |
| 7,596,470 | B2 * | 9/2009 | Kim .............................. | 702/183 |
| 7,672,793 | B2 * | 3/2010 | Beard ............................. | 702/35 |
| 7,946,176 | B2 * | 5/2011 | Liu et al. ......................... | 73/597 |
| 8,046,177 | B2 * | 10/2011 | Liu et al. ......................... | 702/35 |

OTHER PUBLICATIONS

U.S. Appl. No. 12/135,591, filed Jun. 9, 2008, Ihn et al.
U.S. Appl. No. 12/239,144, filed Sep. 26, 2008, Ihn et al.
Giurgiutiu, "Lamb Wave Generation with Piezoelectric Wafer Active Sensors for Structural Health Monitoring", SPIE's 10th annual International Symposium on Smart Structures and Materials, and 8th Annual International Symposium on NDE fro Health Monitoring and Diagnostics, Mar. 2002, San Diego, CA, pp. 1-12.
Degertekin et al., "Single mode Lamb wave excitation in thin plates by Hertzian contacts", 1996 American Institute of Physics, Appl. Phys. Lett. 69 (2) Jul. 8, 1996, pp. 146-148.
Gao et al., "Ultrasonic Guided Wave Annular Array Transducers for Structural Health Monitoring", Review of Quantitative Nondestructive Evaluation vol. 25, ed. D.O. Thompson and D.E. Chimenti, 2006 American Institute of Physics, pp. 1680-1686.

* cited by examiner

*Primary Examiner* — J M Saint Surin
(74) *Attorney, Agent, or Firm* — Yee & Associates, P.C.

(57) ABSTRACT

The different advantageous embodiments provide a transducer unit, a testing system, and a method for testing a structure. The transducer unit comprises a first segment configured to generate a first electrical signal in response to detecting a plurality of waves propagating in a structure. The transducer unit also comprises a second segment configured to generate a second electrical signal in response to detecting the plurality of waves propagating in the structure.

27 Claims, 8 Drawing Sheets

MODE DECOMPOSITION OF SOUND WAVES USING AMPLITUDE MATCHING

BACKGROUND INFORMATION

1. Field

The present disclosure relates generally to testing structures and, in particular, to testing a structure using lamb waves propagating through the structure. Still more particularly, the present disclosure relates to a method and apparatus for identifying lamb wave modes in lamb waves propagating through a structure.

2. Background

Non-destructive inspection of structures for aircraft is performed. The non-destructive inspection is performed to determine whether inconsistencies or changes have occurred within the structures. These structures may be inspected before being assembled or associated with the aircraft during manufacturing of an aircraft. These aircraft are tested to determine whether they meet design parameters for the parts.

Additionally, tests also may be performed on the structures after the structures have been assembled to form the aircraft. This testing may be performed during maintenance or during use of the aircraft.

The inspections may be performed by testing the structure to determine whether a particular structure may need reworking or replacement. This inspection may be performed by setting up equipment in an area to test the structure. The testing also may be performed using health monitoring systems integrated into the structure and/or the aircraft.

The inspection may involve various types of systems, such as ultrasonic systems and x-ray systems. With x-ray systems, x-rays are sent through a structure that is to be tested. Images generated by this transmission of x-rays may be examined to determine whether inconsistencies or changes in the structure have occurred.

With ultrasonic systems, transducers are used to generate signals in the structure. These signals are detected and analyzed to identify the health of the structure. These signals propagating the structure may take the form of lamb waves.

Lamb waves are waves that propagate through a structure. In these examples, lamb waves propagate through a solid structure. Lamb waves are waves with a particle motion that lies in a plane in the structure and the direction of wave propagation. The wave propagation of these types of waves is guided by the boundary of the structure in which they propagate. With lamb waves, these waves have a number of different modes. The modes may include symmetric zero order modes and anti-symmetric zero order modes. These modes exist over larger frequency spectrums, as compared to other types of modes that may be present.

In testing structures, lamb waves may include a number of modes that may be undesirable or unneeded for determining the health of a structure. These other modes may increase the difficulty of interpreting the health of the structure.

These signals detected by the testing system may be interpreted to determine the health of the structure. For example, the data gathered from the tests may be compared to a baseline or a history of data from which the structure was in a condition considered suitable for use. If the test data and the baseline are the same or close enough to each other, the structure may be considered to be healthy. Otherwise, reworking or replacement of the structure may occur. In other test systems, the test data may be used with a model of the structure in a desired condition. This comparison may be used to identify the health of the structure.

Accordingly, it would be advantageous to have a method and apparatus which takes into account one or more of the issues discussed above, as well as possibly other issues.

SUMMARY

In one advantageous embodiment, a transducer unit is presented. The transducer unit comprises a first segment configured to generate a first electrical signal in response to detecting a plurality of waves propagating in a structure. The transducer unit also comprises a second segment configured to generate a second electrical signal in response to detecting the plurality of waves propagating in the structure.

In another advantageous embodiment, a testing system is presented. The testing system comprises a number of transducers in which each transducer unit in the number of transducers comprises a first segment configured to generate a first electrical signal in response to detecting a plurality of waves propagating in a structure and a second segment configured to generate a second electrical signal in response to detecting the plurality of waves propagating in the structure. The first segment has a center and is symmetric about two axes in a direction of wave propagation, and the second segment has a center and is symmetric about the two axes in the direction of the wave propagation. The testing system also comprises a controller configured to receive the first electrical signal and the second electrical signal and process the first electrical signal and the second electrical signal.

In yet another advantageous embodiment, a method for testing a structure is presented. The method detects a plurality of waves propagating in the structure at a number of transducers. Each transducer unit in the number of transducers comprises a first segment configured to generate a first electrical signal in response to detecting the plurality of waves and a second segment configured to generate a second electrical signal in response to detecting the plurality of waves propagating in the structure. The first segment has a center and is symmetric about two axes in a direction of wave propagation, and the second segment has a center and is symmetric about the two axes in the direction of the wave propagation. The method then processes the first electrical signal and the second electrical signal to form a result.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives, and advantages thereof, will best be understood by reference to the following detailed description of an advantageous embodiment of the present disclosure when read in conjunction with the accompanying drawings, wherein:

DETAILED DESCRIPTION

Figure 1:
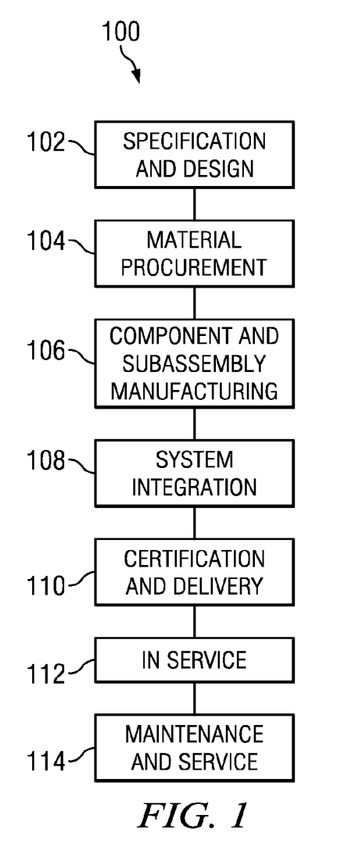
FIG. 1 is an illustration of an aircraft manufacturing and service method in accordance with an advantageous embodiment.
Figure 2:
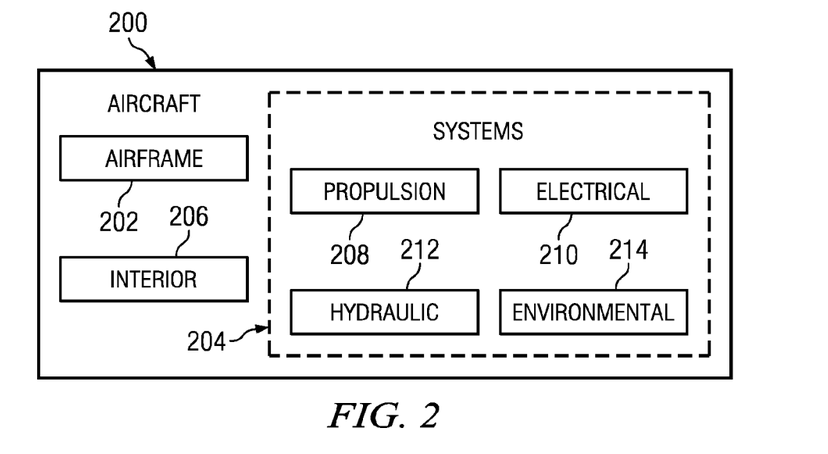
FIG. 2 is an illustration of an aircraft in which an advantageous embodiment may be implemented.

Referring more particularly to the drawings, embodiments of the disclosure may be described in the context of aircraft manufacturing and service method 100 as shown in FIG. 1 and aircraft 200 as shown in FIG. 2. Turning first to FIG. 1, an illustration of an aircraft manufacturing and service method is depicted in accordance with an advantageous embodiment. During pre-production, aircraft manufacturing and service method 100 may include specification and design 102 of aircraft 200 in FIG. 2 and material procurement 104.

During production, component and subassembly manufacturing 106 and system integration 108 of aircraft 200 in FIG. 2 takes place. Thereafter, aircraft 200 in FIG. 2 may go through certification and delivery 110 in order to be placed in service 112. While in service 112 by a customer, aircraft 200 in FIG. 2 is scheduled for routine maintenance and service 114, which may include modification, reconfiguration, refurbishment, and other maintenance or service.

Portions of aircraft 200 may be tested for inconsistencies during production, component and subassembly manufacturing 106, and system integration 108 of aircraft 200. The testing may be performed to determine whether portions of aircraft 200 meet a number of desired specifications.

The number of desired specifications may include a minimum strength of the portions of aircraft 200. That is, the number of desired specifications may indicate that portions of aircraft 200 are to sustain a particular amount of force applied to the portions without an inconsistency developing in the portions. Of course, the testing may also occur during maintenance and service 114 to determine whether portions in service 112 continue to meet the number of desired specifications.

Each of the processes of aircraft manufacturing and service method 100 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of venders, subcontractors, and suppliers; and an operator may be an airline, leasing company, military entity, service organization, and so on.

With reference now to FIG. 2, an illustration of an aircraft is depicted in which an advantageous embodiment may be implemented. In this example, aircraft 200 is produced by aircraft manufacturing and service method 100 in FIG. 1 and may include airframe 202 with a plurality of systems 204 and interior 206. Examples of systems 204 include one or more of propulsion system 208, electrical system 210, hydraulic system 212, and environmental system 214. Any number of other systems may be included. Although an aerospace example is shown, different advantageous embodiments may be applied to other industries, such as the automotive industry.

Apparatus and methods embodied herein may be employed during at least one of the stages of aircraft manufacturing and service method 100 in FIG. 1. As used herein, the phrase "at least one of", when used with a list of items, means that different combinations of one or more of the listed items may be used and only one of each item in the list may be needed. For example, "at least one of item A, item B, and item C" may include, for example, without limitation, item A or item A and item B. This example also may include item A, item B, and item C or item B and item C.

In one illustrative example, components or subassemblies produced in component and subassembly manufacturing 106 in FIG. 1 may be fabricated or manufactured in a manner similar to components or subassemblies produced while aircraft 200 is in service 112 in FIG. 1. As yet another example, a number of apparatus embodiments, method embodiments, or a combination thereof may be utilized during production stages, such as component and subassembly manufacturing 106 and system integration 108 in FIG. 1. A number, when referring to items, means one or more items. For example, a number of apparatus embodiments is one or more apparatus embodiments. A number of apparatus embodiments, method embodiments, or a combination thereof may be utilized while aircraft 200 is in service 112 and/or during maintenance and service 114 in FIG. 1. The use of a number of the different advantageous embodiments may substantially expedite the assembly of and/or reduce the cost of aircraft 200.

The different advantageous embodiments recognize and take into account a number of different considerations. For example, the different advantageous embodiments recognize that one solution for obtaining a desired mode in signals without other modes may involve exciting transducers at selected frequencies or using transducers with a particular size in which a desired mode is dominant or most likely to be detected. In this way, desired modes may be identified during testing.

The different advantageous embodiments recognize and take into account another solution that may involve selecting the spacing of the transducers and applying a time delay. The time delay is applied to a set of transducers in a manner that generates a desired mode. The different advantageous embodiments also recognize and take into account that a desired mode can be generated by applying sheer and/or longitudinal traction at the edge or surface of a structure, such as a plate.

The different advantageous embodiments recognize and take into account that these solutions are capable of generating the desired modes for analysis. The different advantageous embodiments also recognize and take into account that these solutions, however, may not have the desired flexibility for isolating the desired modes at any frequency that may be used for different sized transducers and/or transducers at different distances apart.

Thus, the different advantageous embodiments provide a method and apparatus for generating signals in a structure. In one advantageous embodiment, a transducer unit comprises a first segment configured to generate an electrical signal in response to detecting a vibration and a second segment configured to generate a second electrical signal in response to detecting the vibration.

Figure 3:
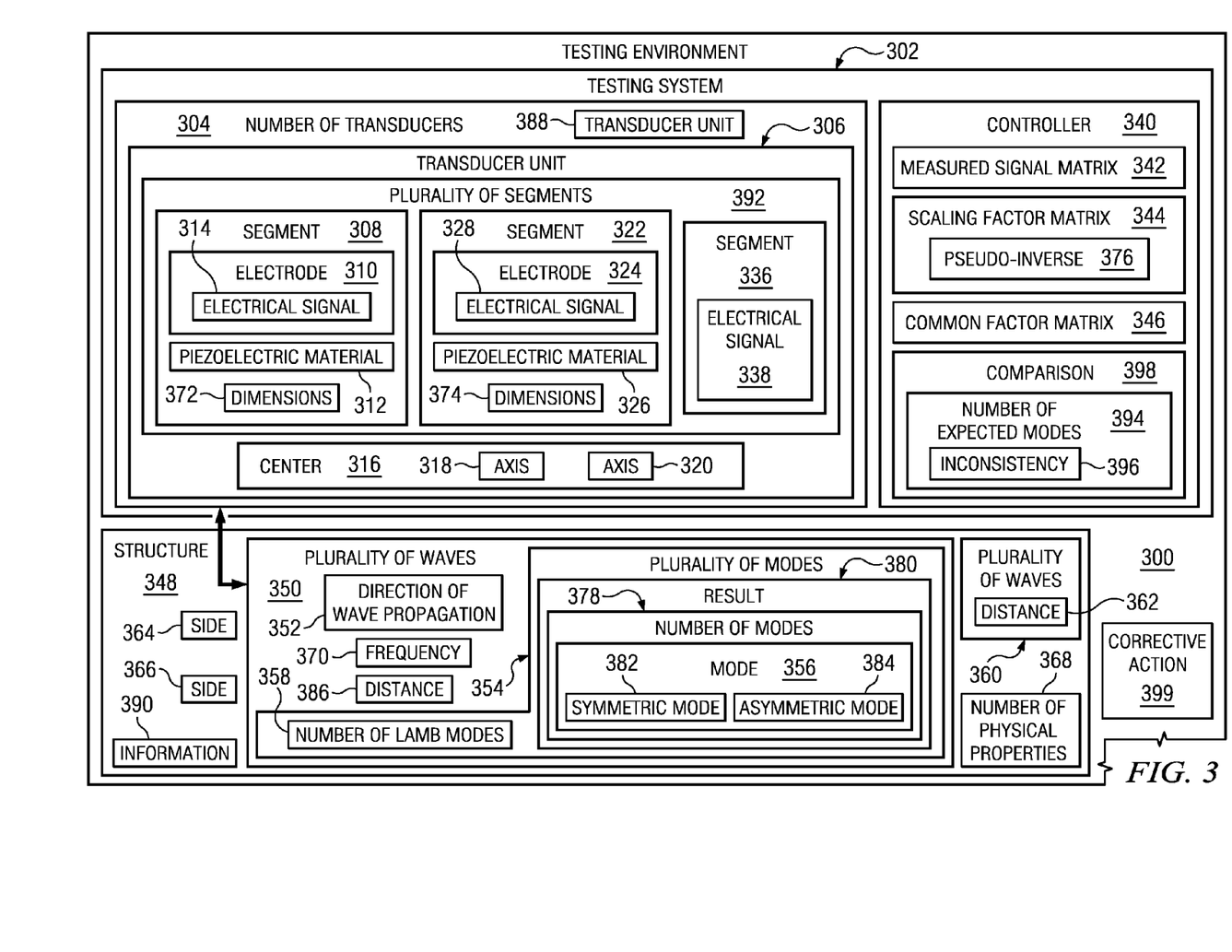
FIG. 3 is an illustration of a testing environment in accordance with an advantageous embodiment.

Turning now to FIG. 3, an illustration of a testing environment is depicted in accordance with an advantageous embodiment. Testing environment 300 may be implemented, for example, within aircraft 200 in FIG. 2. Testing using testing environment 300 may be performed during component and subassembly manufacturing 106 and/or maintenance and service 114 in FIG. 1.

Testing environment 300 is an environment in which testing system 302 obtains information 390 from structure 348. Testing system 302 obtains information 390 from structure 348 by exciting structure 348 such that plurality of waves 350 is generated in structure 348. Obtaining information 390 may comprise testing for a number of inconsistencies. Structure 348 is a solid material. Structure 348 may be composed of a number of layers. Structure 348 may be, for example, any combination of metal, plastic, a composite material, and/or other suitable materials.

Testing system 302 may be associated with structure 348 when obtaining information 390. Alternatively, testing system 302 may be associated with structure 348 during routine use of structure 348. In other words, testing system 302 may become dissociated from structure 348 after information 390 is obtained, or testing system 302 may be associated with structure 348 to monitor structure 348 constantly or periodically. For example, structure 348 may be constantly or periodically monitored using testing system 302 in an advantageous embodiment in which testing system 302 is a portion of a health monitoring system for a platform containing structure 348.

Plurality of waves 350 travel through structure 348 and are detected by testing system 302. Plurality of waves 350 are detected using transducer unit 306. Transducer unit 306 is a device that converts one type of energy to another. In these examples, transducer unit 306 converts energy in plurality of waves 350 to electrical signal 314.

Transducer unit 306 comprises plurality of segments 392. In these illustrative examples, plurality of segments 392 includes segment 308 and segment 322. Segment 336 is also present in some advantageous embodiments. Segment 308 contacts structure 348 to detect plurality of waves 350 in structure 348. In another advantageous embodiment, segment 308 is positioned on side 364 of structure 348. Segment 308 has center 316 and has a size described by dimensions 372. Center 316 is the centrally located point of segment 308. Dimensions 372 are the size of the portion of segment 308 that detects plurality of waves 350.

In some advantageous embodiments, dimensions 372 of segment 308 are such that segment 308 is symmetrical along axis 318 and axis 320. Axis 318 and axis 320 may pass through center 316. For example, segment 308 may be an oval shape that is symmetrical along both axis 318 and axis 320. Of course, segment 308 may be another shape. Segment 308 may be a square shape, a circular shape, a rectangular shape, or another suitable shape.

Segment 308 comprises electrode 310 and piezoelectric material 312. Electrode 310 is a conductor through which a current enters or leaves a non-metallic medium. Electrode 310 may be made of a metallic or non-metallic substance. In these examples, electrode 310 comprises nickel. Electrode 310 is positioned on side 364 and side 366 of structure 348. When plurality of waves 350 is propagated through structure 348, piezoelectric material 312 detects plurality of waves 350. In response to detecting plurality of waves 350, piezoelectric material 312 generates electrical signal 314 and transfers electrical signal 314 to electrode 310. In this way, segment 308 acts as a sensor.

Piezoelectric material 312 is a material that generates electrical signal 314 in response to detecting a mechanical force. For example, piezoelectric material 312 may be at least one of quartz, topaz, tourmaline, barium titanate, sodium tungstate, and/or other suitable materials.

Alternatively, segment 308 may act as an actuator. That is, segment 308 may use piezoelectric material 312 to convert electrical signal 314 to propagate plurality of waves 350 in structure 348. In one advantageous embodiment, segment 308 acts as an actuator, and segment 322 acts as a sensor. In such an embodiment, segment 308 excites structure 348 to generate plurality of waves 350 in structure 348. Segment 322 then generates electric signal 328 in response to detecting plurality of waves 350.

Segment 322 may comprise the same types of components as segment 308. For example, segment 322 may comprise electrode 324 and piezoelectric material 326. The size of segment 322 may be described using dimensions 374. Segment 322 is positioned such that segment 322 also has center 316. That is, both segment 308 and segment 322 have center 316.

Segment 308 and segment 322 may also be symmetrical along both axis 318 and axis 320. For example, segment 308 may be an oval, and segment 322 may be an oval ring that encloses segment 308. Segment 308 may be symmetrical along axis 318 and axis 320. Segment 322 may also be symmetrical along axis 318 and axis 320. A gap may be present between segment 308 and segment 322. Segment 308 and/or segment 322 may detect plurality of waves 350 when direction of wave propagation 352 is substantially the same as axis 318 and/or axis 320. In other words, segment 308 and/or segment 322 may not detect plurality of waves 350 unless direction of wave propagation 352 is substantially the same as an axis along which segment 308 and/or segment 322 are symmetrical.

In some advantageous embodiments, transducer unit 306 also comprises segment 336. Segment 336 may be a segment like segment 308 and/or segment 322. Segment 336 may also generate electrical signal 338 in response to detecting plurality of waves 350. In other advantageous embodiments, segment 336 is absent.

In yet other advantageous embodiments, number of transducers 304 also comprises transducer unit 388. Transducer unit 388 may comprise a number of segments, such as segment 308 and/or segment 322. In such advantageous embodiments, controller 340 records measurements of electrical signal 314, electrical signal 328, and electrical signal 338 generated by transducer unit 388.

Segment 308 in transducer unit 306 and transducer unit 388 may act as a sensor, while segment 322 in transducer unit 306 and transducer unit 388 acts as an actuator. Controller 340 stores measurements for a number of actuator and sensor combinations. In one advantageous embodiment, controller 340 stores measurements for all combinations of segments within transducer unit 306 and transducer unit 388.

Plurality of waves 350 comprises plurality of modes 354. Plurality of modes 354 is the type of waves contained within plurality of waves 350. That is, plurality of modes 354 is the various patterns of oscillation that occur within the structure due to the propagation of plurality of waves 350. For example, plurality of modes 354 may comprise longitudinal, shear, surface, and number of Lamb modes 358.

Number of Lamb modes 358 comprises a zero-order symmetrical mode, a zero-order asymmetrical mode, and higher order modes. The zero-order symmetrical mode and the zero-order asymmetrical mode may be used to determine whether an inconsistency is present in structure 348 by comparing the zero-order asymmetrical and/or zero-order symmetrical mode to a previous measurement or a modeled measurement.

The zero-order symmetrical mode and the zero-order asymmetrical mode may carry more energy than the higher-order modes. The zero-order symmetrical mode and the zero-order asymmetrical mode may also be present within plurality of waves 350 across frequency 370. Frequency 370 is the frequency used by segment 308 to propagate plurality of waves 350 when segment 308 acts as an actuator. In one advantageous embodiment, plurality of waves 350 comprises both a zero-order symmetrical mode and a zero-order asymmetrical mode.

Result 380 is number of modes 378 in plurality of modes 354. Result 380 is the result data obtained from testing system 302 on structure 348. Number of modes 378 is a subset of plurality of modes 354. That is, number of modes 378 is obtained from plurality of modes 354 by determining an effect on plurality of waves 350 by number of modes 378. In one advantageous embodiment, number of modes 378 is mode 356. In such an advantageous embodiment, result 380 of testing system 302 on structure 348 is mode 356. Mode 356 may be symmetric mode 382 or asymmetric mode 384.

Once electrical signal 314 and/or electrical signal 328 are generated in segment 308 and/or segment 322, testing system 302 obtains result 380 using controller 340. In order to obtain result 380, controller 340 forms the following equation:

$$\begin{Bmatrix} F_{11} \\ F_{12} \\ F_{13} \\ F_{21} \\ F_{22} \\ F_{23} \\ F_{31} \\ F_{32} \\ F_{33} \end{Bmatrix} = \begin{bmatrix} S_{11} & A_{11} \\ S_{12} & A_{12} \\ S_{13} & A_{13} \\ S_{21} & A_{21} \\ S_{22} & A_{22} \\ S_{23} & A_{23} \\ S_{31} & A_{31} \\ S_{32} & A_{32} \\ S_{33} & A_{33} \end{bmatrix} \begin{bmatrix} M_{S_0} \\ M_{A_0} \end{bmatrix}$$

The $F_{ij}$ matrix represents measured signal matrix 342, where i is the segment or segments acting as an actuator and j is the segment or segments acting as a sensor for the test. Controller 340 creates measured signal matrix 342 using electrical signal 314 and/or electrical signal 328. Measured signal matrix 342 is a matrix containing the measurements recorded for electrical signal 314 and/or electrical signal 328. Measured signal matrix 342 may contain measurements representing periods in which segment 308 acted as a sensor and segment 322 acted as an actuator, as well as periods in which segment 308 acted as an actuator and segment 322 acted as a sensor. Electrical signal 314 and electrical signal 328 may be stored in measured signal matrix 342 as functions of voltage over time.

The $S_{ij}$, $A_{ij}$ matrix represents scaling factor matrix 344. Scaling factor matrix 344 scales the amplitude of common factor matrix 346 to become measured signal matrix 342 when scaling factor matrix 344 is multiplied by common factor matrix 346. Scaling factor matrix 344 comprises real numbers. In this advantageous embodiment, scaling factor matrix 344 contains values for both symmetric and asymmetric modes.

In one advantageous embodiment, scaling factor matrix 344 is predicted by controller 340 using number of physical properties 368 of structure 348, frequency 370, dimensions 372, and dimensions 374. Number of physical properties 368 may be physical characteristics of structure 348. For example, number of physical properties 368 may be conductivity of structure 348, dimensions and/or thickness of structure 348, and density of structure 348. Frequency 370 is the frequency used by segment 308 to propagate plurality of waves 350 in structure 348.

In another advantageous embodiment, scaling factor matrix 344 is identified by performing a baseline test on structure 348. A baseline test is a test performed on structure 348 that allows mode 356 to be identified within plurality of modes 354. In an advantageous embodiment, structure 348 has side 364 and side 366. The baseline test may be performed by associating transducer unit 306 with side 364 and transducer unit 388 with side 366. For example, transducer unit 306 may be connected to side 364, and transducer unit 388 may be connected to side 366.

Alternatively, transducer unit 306 and transducer unit 388 may be associated with structure 348 on side 364 at least distance 362 apart. Distance 362 is based on number of physical properties 368 for structure 348. In one advantageous embodiment, distance 362 is greater than distance 386.

A first component is considered to be associated with a second component by being secured to the second component, bonded to the second component, fastened to the second component, and/or connected to the second component in some other suitable manner. The first component also may be connected to the second component by using a third component. The first component is also considered to be associated with the second component by being formed as part of and/or an extension of the second component.

The baseline test comprises propagating plurality of waves 360 through structure 348. The baseline test further comprises measuring electrical signal 314 and/or electrical signal 328 for the various sensor actuator combinations. When the baseline test is performed using side 364 and side 366, electrical signal 314 for each sensor actuator combination is mode 356. Mode 356 may be a function of voltage over time. Controller 340 then identifies a multiplier that equalizes mode 356 across the different sensor actuator combinations. The multipliers are then stored as scaling factor matrix 344. The multipliers may be used as scaling factor matrix 344, because the relationship between the multipliers remains substantially constant throughout structure 348.

The $$\begin{bmatrix} M_{S_0} \\ M_{A_0} \end{bmatrix}$$

matrix represents number of modes 378 as common factor matrix 346. That is, common factor matrix 346 comprises the response of number of modes 378 to plurality of waves 350. This response is identified by solving common factor matrix 346 in the following equation:

$$\begin{Bmatrix} F_{11} \\ F_{12} \\ F_{13} \\ F_{21} \\ F_{22} \\ F_{23} \\ F_{31} \\ F_{32} \\ F_{33} \end{Bmatrix} = \begin{bmatrix} S_{11} & A_{11} \\ S_{12} & A_{12} \\ S_{13} & A_{13} \\ S_{21} & A_{21} \\ S_{22} & A_{22} \\ S_{23} & A_{23} \\ S_{31} & A_{31} \\ S_{32} & A_{32} \\ S_{33} & A_{33} \end{bmatrix} \begin{bmatrix} M_{S_0} \\ M_{A_0} \end{bmatrix}$$

In an advantageous embodiment, controller 340 solves common factor matrix 346 by performing pseudo-inverse 376 of scaling factor matrix 344. Pseudo-inverse 376 is a generalization of the inverse matrix. That is, pseudo-inverse 376 is a matrix function that creates a matrix with particular properties of the inverse of the matrix but can be applied to matrices that are non-invertible.

Once pseudo-inverse 376 is applied, controller 340 premultiplies scaling factor matrix 344 with measured signal matrix 342. Number of modes 378 may then be identified for a particular i,j combination. That is, number of modes 378 may be identified for each sensor actuator combination. Number of modes 378 may be presented as a function of voltage over time.

In some advantageous embodiments, number of modes 378 is then compared to number of expected modes 394 in comparison 398. Number of expected modes 394 may be identified using a measurement made in the past or using a model. In an advantageous embodiment, number of expected modes 394 is identified using a measurement made at a time it was believed there was no inconsistency 396 in the structure. In another advantageous embodiment, the measurement was made at a time there was no inconsistency 396 deemed unacceptable. In other words, inconsistency 396 may be present, but inconsistency 396 does not cause structure 348 to fall outside of a specification for the structure.

Number of expected modes 394 may also be identified using a model. The model may generate number of expected modes 394 using number of physical properties 368 of structure 348, frequency 370 of plurality of waves 350, and dimensions 372 of plurality of segments 392.

Controller 340 may then determine whether inconsistency 396 is present based on comparison 398. Controller 340 may determine that inconsistency 396 is present if number of modes 378 differs from number of expected modes 394 by a specified amount.

When controller 340 determines that inconsistency 396 is present in structure 348, controller 340 may perform corrective action 399. In some illustrative embodiments, corrective action 399 is performed at least partially by a human. For example, corrective action 399 may be writing to a log, sending an alert, reworking structure 348, or replacing structure 348.

The illustration of testing system 302 in testing environment 300 is not meant to imply physical or architectural limitations to the manner in which different features may be implemented. Other components in addition to and/or in place of the ones illustrated may be used. Some components may be unnecessary in some advantageous embodiments. Also, the blocks are presented to illustrate some functional components. One or more of these blocks may be combined and/or divided into different blocks when implemented in different advantageous embodiments.

For example, in some advantageous embodiments, number of transducers 304 comprises additional transducer units, such as transducer unit 306. Controller 340 may further comprise a processor unit and/or a number of storage devices for performing matrix operations on measured signal matrix 342, scaling factor matrix 344, and common factor matrix 346. Testing system 302 may also comprise a communications unit. The communications unit may be used to transmit number of modes 378 for future analysis and/or storage.

Additionally, plurality of segments 392 may comprise any quantity of segment 308. In some illustrative examples, plurality of segments 392 comprises segment 308 and segment 322. In other illustrative examples, plurality of segments 392 comprises segment 308, segment 322, and segment 336. However, the quantity of segments in plurality of segments 392 may be more or less.

Figure 4:
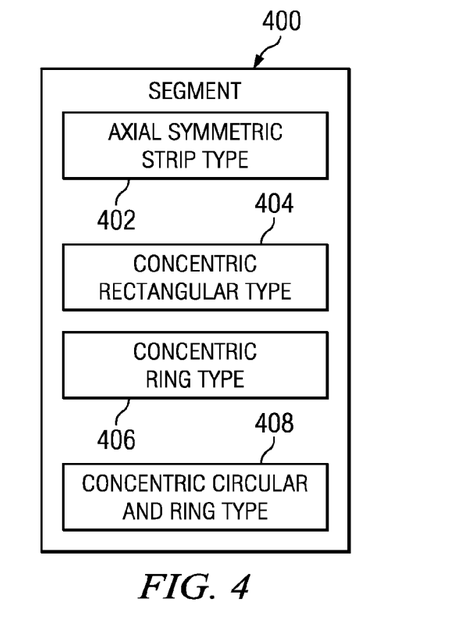
FIG. 4 is an illustration of a segment in accordance with an advantageous embodiment.

Turning now to FIG. 4, an illustration of a segment is depicted in accordance with an advantageous embodiment. Segment 400 comprises a number of example implementations of segment 308 and/or segment 322 in FIG. 3.

Segment 400 may be one of a number of types. In one advantageous embodiment, segment 400 is axial symmetric strip type 402. Segment 400 of axial symmetric strip type 402 is symmetric about an axis that runs centrally through segment 400. Segment 400 also comprises a number of strips. That is, segment 400 comprises a number of rectangles that are symmetrical about the axis. A number of gaps may be present between the number of rectangles.

In another advantageous embodiment, segment 400 of concentric rectangular type 404 comprises a rectangular segment that surrounds a second rectangular segment. In such an advantageous embodiment, segment 400 is symmetrical across two axes. A gap may exist between the two rectangular segments.

In yet another advantageous embodiment, segment 400 of concentric ring type 406 comprises a circular ring segment that surrounds a second circular ring segment. In such an advantageous embodiment, segment 400 may detect waves traveling in any direction, because segment 400 is symmetrical in every direction. A gap may exist between the two circular ring segments. A gap may also exist within the second circular ring segment.

In yet another advantageous embodiment, segment 400 of concentric circular and ring type 408 comprises a circular ring segment that surrounds a circular segment. In such an advantageous embodiment, segment 400 may detect waves traveling in any direction because segment 400 is symmetrical in every direction. A gap may exist between the circular ring segment and the circular segment.

While several types for segment 400 are depicted, it should be noted that segment 400 may take any other suitable form and should not be limited to those types described in these illustrative examples.

Figure 5:
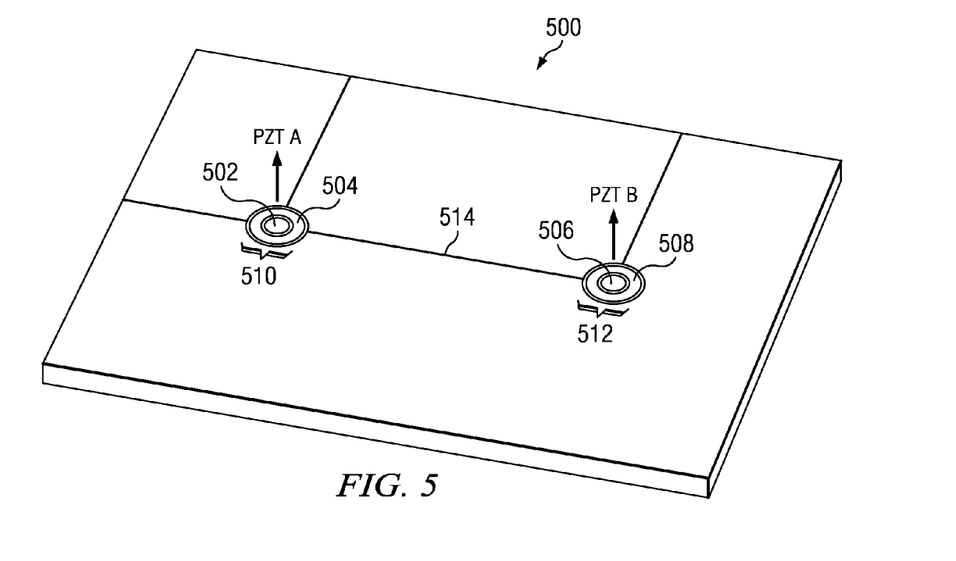
FIG. 5 is an illustration of a structure under test in accordance with an advantageous embodiment.

Turning now to FIG. 5, an illustration of a structure under test is depicted in accordance with an advantageous embodiment. Structure 500 is an example implementation of structure 348 in FIG. 3. In this example, structure 500 is being tested by a testing system, such as testing system 302 in FIG. 3.

Structure 500 is being tested by transducer 510 and transducer 512. Transducer 510 and transducer 512 are positioned over structure 500. Transducer 510 comprises segment 502 and segment 504. Transducer 512 comprises segment 506 and segment 508. In this advantageous embodiment, the testing system propagates waves through surface 500 at an actuator segment. For example, segment 508 may be selected as an actuator. The testing system then detects the waves at each other segment. In this advantageous embodiment, the testing system will detect the waves using segment 502, segment 504, and segment 506.

In some advantageous embodiments, both segments 502 and 504 of transducer 510 are used as a sensor or an actuator. The electric signals may be recorded and/or stored as a function of voltage over time.

In another advantageous embodiment, the test being performed on structure 500 is a baseline test. In such an embodiment, distance 514 between transducer 510 and transducer 512 may be at least a particular distance at which the effect of a particular mode or a particular number of modes may be identified in the electric signals. Alternatively, the baseline test may comprise positioning either transducer 510 or transducer 512 on the bottom of structure 500.

Figure 6:
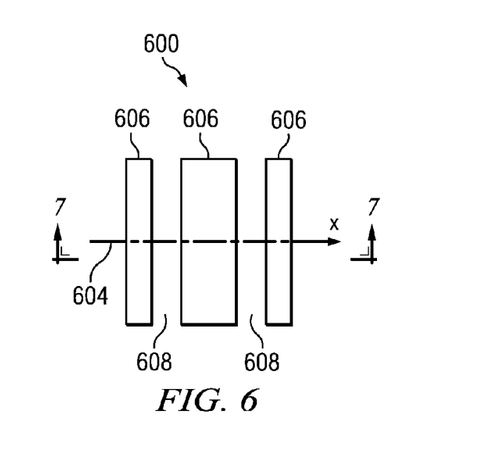
FIG. 6 is an illustration of a surface of an axial symmetric strip type segment in accordance with an advantageous embodiment.
Figure 7:
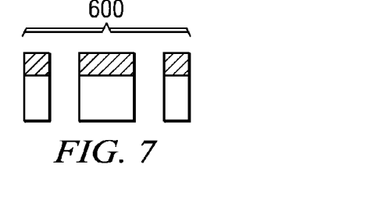
FIG. 7 is an illustration of a cross-sectional view of an axial symmetric strip type segment in accordance with an advantageous embodiment.

Turning now to FIGS. 6-7, illustrations of an axial symmetric strip type segment are depicted in accordance with an advantageous embodiment. FIG. 6 depicts a surface of an axial symmetric strip type segment in accordance with an advantageous embodiment.

Axial symmetric strip type segment 600 is an example implementation of axial symmetric strip type 402 in FIG. 4. Axial symmetric strip type segment 600 comprises segments 606 that are symmetrical about axis 604. Segments 606 are positioned on a side of a structure to obtain information by engaging segments 606 as sensors and/or actuators. In this advantageous embodiment, gaps 608 are present between the number of rectangles in axial symmetric strip type segment 600.

FIG. 7 depicts a cross-sectional view of axial symmetric strip type segment 600 in accordance with an advantageous embodiment. In this illustration, axial symmetric strip type segment 600 is depicted as being taken along line 7-7 in FIG. 6.

Figure 8:
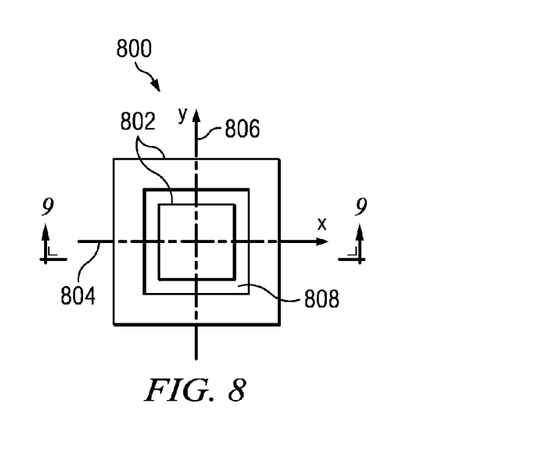
FIG. 8 is an illustration of a surface of a concentric rectangle type segment in accordance with an advantageous embodiment.
Figure 9:
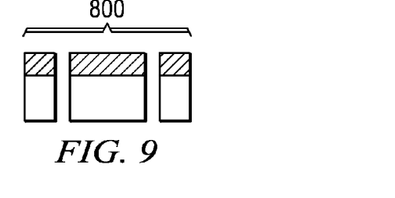
FIG. 9 is an illustration of a cross-sectional view of a concentric rectangle type segment in accordance with an advantageous embodiment.

Turning now to FIGS. 8-9, illustrations of a concentric rectangle type segment are depicted in accordance with an advantageous embodiment. FIG. 8 depicts a surface of a concentric rectangle type segment in accordance with an advantageous embodiment.

Concentric rectangle type segment 800 is an example implementation of concentric rectangular type 404 in FIG. 4. Concentric rectangle type segment 800 comprises segments 802 that are symmetrical about axis 804 and axis 806. Segments 802 are positioned on a side of a structure to obtain information by engaging segments 802 as sensors and/or actuators. In this advantageous embodiment, gap 808 is present between segments 802 in concentric rectangle type segment 800.

FIG. 9 depicts a cross-sectional view of concentric rectangle type segment 800 in accordance with an advantageous embodiment. In this illustration, concentric rectangle type segment 800 is depicted as being taken along line 9-9 in FIG. 8.

Figure 10:
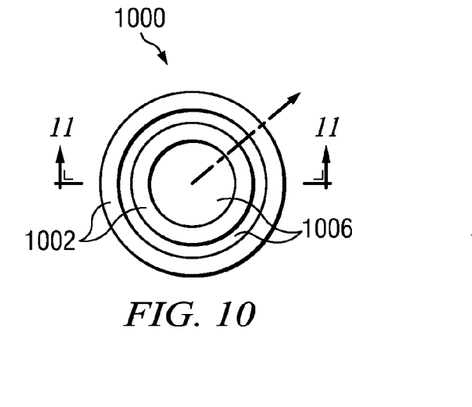
FIG. 10 is an illustration of a surface of a concentric ring type segment in accordance with an advantageous embodiment.
Figure 11:
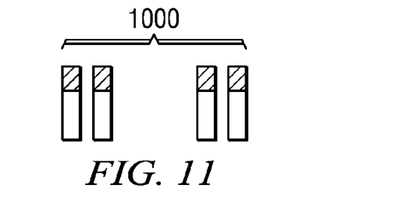
FIG. 11 is an illustration of a cross-sectional view of a concentric ring type segment in accordance with an advantageous embodiment.

Turning now to FIGS. 10-11, illustrations of a concentric ring type segment are depicted in accordance with an advantageous embodiment. FIG. 10 depicts a surface of a concentric ring type segment in accordance with an advantageous embodiment.

Concentric ring type segment 1000 is an example implementation of concentric ring type 406 in FIG. 4. Concentric ring type segment 1000 comprises segments 1002 that form a first ring surrounding a second ring. Segments 1002 are positioned on a side of a structure to obtain information by engaging segments 1002 as sensors and/or actuators. In this advantageous embodiment, gaps 1006 are present between segments 1002 in concentric ring type segment 1000.

FIG. 11 depicts a cross-sectional view of concentric ring type segment 1000 in accordance with an advantageous embodiment. In this illustration, concentric ring type segment 1000 is depicted as being taken along line 11-11 in FIG. 10.

Figure 12:
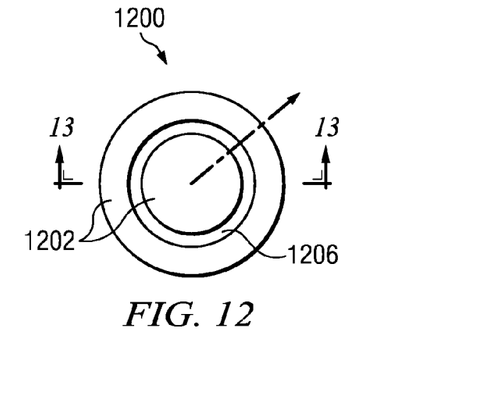
FIG. 12 is an illustration of a surface of a concentric circular and ring type segment in accordance with an advantageous embodiment.
Figure 13:
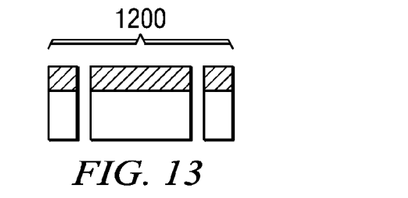
FIG. 13 is an illustration of a cross-sectional view of a concentric circular and ring type segment in accordance with an advantageous embodiment.

Turning now to FIGS. 12-13, illustrations of a concentric circular and ring type segment are depicted in accordance with an advantageous embodiment. FIG. 12 depicts a surface of a concentric circular and ring type segment in accordance with an advantageous embodiment.

Concentric circular and ring type segment 1200 is an example implementation of concentric circular and ring type 408 in FIG. 4. Concentric circular and ring type segment 1200 comprises segments 1202. In this example, segments 1202 are ring segments that surround a circular segment. Segments 1202 are positioned on a side of a structure to obtain information by engaging segments 1202 as sensors and/or actuators. In this advantageous embodiment, gap 1206 is present between segments 1202 in concentric circular and ring type segment 1200.

FIG. 13 depicts a cross-sectional view of concentric circular and ring type segment 1200 in accordance with an advantageous embodiment. In this illustration, concentric circular and ring type segment 1200 is depicted as being taken along line 13-13 in FIG. 12.

Figure 14:
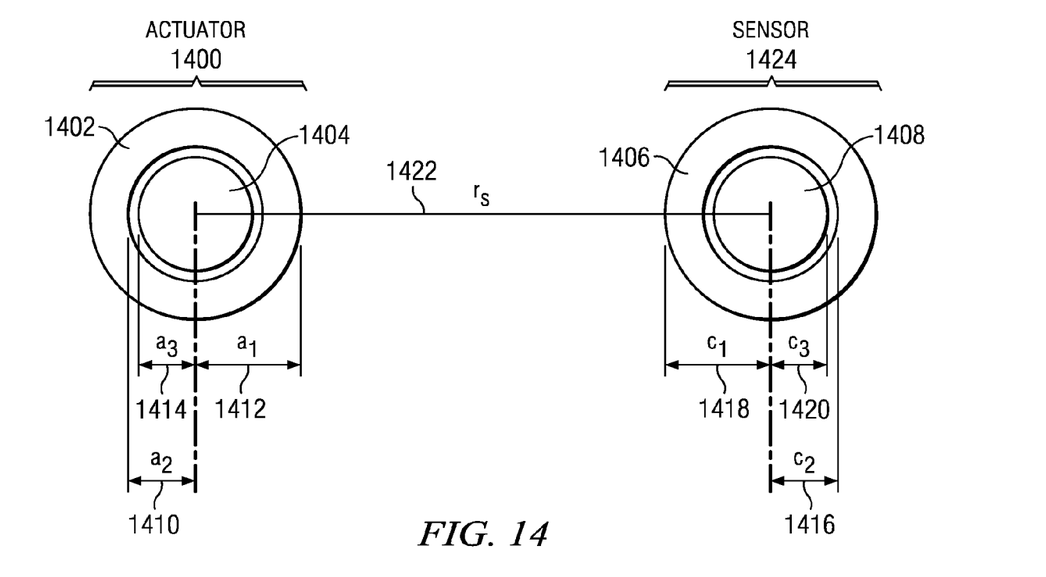
FIG. 14 is an illustration of an actuator and a sensor in accordance with an advantageous embodiment.

Turning now to FIG. 14, an illustration of an actuator and a sensor are depicted in accordance with an advantageous embodiment. Transducer 1400 and transducer 1424 are example implementations of transducer unit 306 and transducer unit 388 in FIG. 3. Segment 1402, segment 1404, segment 1406, and segment 1408 are example implementations of segment 308 and segment 322 in FIG. 3.

Transducer 1400 and transducer 1424 are separated by distance $r_s$ 1422. Distance $r_s$ 1422 is a distance between transducer 1400 and transducer 1424 on a structure being tested. Distance $r_s$ 1422 is an example implementation of distance 386 in FIG. 3.

Radius $a_1$ 1412 is a radius of transducer 1400. Radius $a_1$ 1412 includes the distance from the center of segment 1404 to the outer edge of segment 1402. Radius $a_2$ 1410 is a radius from the center of segment 1404 to the inner edge of segment 1402. Radius $a_3$ 1414 is a radius from the center of segment 1404 to the outer edge of segment 1404.

Radius $c_1$ 1418 is a radius of transducer 1424. Radius $c_1$ 1418 includes the distance from the center of segment 1408 to the outer edge of segment 1406. Radius $c_2$ 1416 is a radius from the center of segment 1408 to the inner edge of segment 1406. Radius $c_3$ 1420 is a radius from the center of segment 1408 to the outer edge of segment 1406.

In this advantageous embodiment, transducer 1400 is acting as an actuator and transducer 1424 is acting as a sensor. Transducer 1400 is excited to generate the waves in the structure using the electric signal. When transducer 1400 is excited and transducer 1424 detects the waves, an output voltage is produced. The output voltage is determined by the size of transducer 1400 acting as an actuator and the size of transducer 1424 acting as a sensor. When a circular actuator having a radius of "a" is excited and a circular sensor having a radius of "c" provides a response signal, the output voltage, v, is as follows:

$$v = -i \frac{a\tau_0 E_s h_s g_{31}}{\mu c}$$

$$e^{i\omega t}\left[\mathcal{J}_1(\xi^{S_0}a)\frac{N_S(\xi^{S_0})}{D'_S(\xi^{S_0})}\int_{r_s-c}^{r_s+c}\left\{\frac{\xi^{S_0} r H_0^{(2)}(\xi^{S_0}r) 2\tan^{-1}}{\left(\sqrt{\frac{4r^2 r_s^2}{([r^2+r_s^2-c^2)]^2}-1}\right)}\right\}dr\right]$$

where $$\alpha^2 = \frac{\omega^2}{c_L^2} - \xi^2; \quad \beta^2 = \frac{\omega^2}{c_T^2} - \xi^2; \quad c_L = \sqrt{\frac{\lambda+2\mu}{\rho}}; \quad c_T = \sqrt{\frac{\mu}{\rho}}$$

$$N_S(\xi) = \xi\beta(\xi^2+\beta^2)\cos\alpha b\cos\beta b;$$

$$D_S(\xi) = ([\xi^2-\beta^2)]^2\cos\alpha b\sin\beta b + 4\xi^2\alpha\beta\sin\alpha b\cos\beta b$$

$$N_A(\xi) = \xi\beta(\xi^2+\beta^2)\sin\alpha b\sin\beta b;$$

$$D_A(\xi) = ([\xi^2-\beta^2)]^2\sin\alpha b\cos\beta b + 4\xi^2\alpha\beta\cos\alpha b\sin\beta b$$

$\lambda$ and $\mu$ are Lamé constants for the structure material, and $E_s$, $h_s$ and $g_{31}$ are Young's modulus, the sensor thickness, and piezoelectric constant, respectively. In this example, M, E, and D are introduced to simplify output signals obtained from actuator and sensor combinations. Note that only the zero-order symmetric mode, such as symmetric mode 382 in FIG. 3, is being described below:

$$M_{S_0} = -i\frac{\tau_0 E_s h_s g_{31}\xi^{S_0}}{\mu}\frac{N_S(\xi^{S_0})}{D'_S(\xi^{S_0})}e^{i\omega t}$$

$$E_i^{S_0} = a_i\mathcal{J}_1(\xi^{S_0}a_i), \quad i=1,2,3$$

$$D_j^{S_0} = \frac{1}{c_j^2}\int_{r_s-c_j}^{r_s+c_j}\left\{rH_0^{(2)}(\xi^{S_0}r)2\tan^{-1}\left(\sqrt{\frac{4r^2 r_s^2}{(r^2-r_s^2-c_j^2)^2}-1}\right)\right\}dr,$$

$$j=1,2,3$$

The output voltages from the nine different actuator and sensor combinations of transducer 1400 and transducer 1424 become:

$$F_{13}^{S_0} = M_{S_0}[E_1^{S_0}D_3^{S_0} - E_2^{S_0}D_3^{S_0} + E_3^{S_0}D_3^{S_0}]$$

-continued $$F_{23}^{S_0} = M_{S_0}[E_3^{S_0}D_3^{S_0} - E_2^{S_0}D_3^{S_0}]$$

$$F_{33}^{S_0} = M_{S_0}E_3^{S_0}D_3^{S_0}$$

$$F_{32}^{S_0} = M_{S_0}\left[\frac{A_1+A_2-A_3}{A_1-A_3}\times E_3^{S_0}D_1^{S_0} - \frac{A_2}{A_1-A_3}\times E_3^{S_0}D_2^{S_0}\right]$$

$$F_{22}^{S_0} = M_{S_0}\left[\begin{array}{c}\frac{A_1+A_2-A_3}{A_1-A_3}\times E_1^{S_0}D_1^{S_0} - \frac{A_2}{A_1-A_3}\times E_1^{S_0}D_2^{S_0} - \\ \frac{A_1+A_2-A_3}{A_1-A_3}\times E_2^{S_0}D_1^{S_0} + \frac{A_2}{A_1-A_3}\times E_2^{S_0}D_2^{S_0}\end{array}\right]$$

$$F_{12}^{S_0} = M_{S_0}\left[\begin{array}{c}\frac{A_1+A_2-A_3}{A_1-A_3}\times E_1^{S_0}D_1^{S_0} - \frac{A_2}{A_1-A_3}\times E_1^{S_0}D_2^{S_0} - \\ \frac{A_1+A_2-A_3}{A_1-A_3}\times E_2^{S_0}D_1^{S_0} + \frac{A_2}{A_1-A_3}\times E_2^{S_0}D_2^{S_0} + \\ \frac{A_1+A_2-A_3}{A_1-A_3}\times E_3^{S_0}D_1^{S_0} - \frac{A_2}{A_1-A_3}\times E_3^{S_0}D_2^{S_0}\end{array}\right]$$

$$F_{31}^{S_0} = M_{S_0}\left[\frac{A_1-A_3}{A_1}F_{32} + \frac{A_3}{A_1}F_{33}\right]$$

$$F_{21}^{S_0} = M_{S_0}\left[\frac{A_1-A_3}{A_1}F_{22} + \frac{A_3}{A_1}F_{23}\right]$$

$$F_{11}^{S_0} = M_{S_0}\left[\frac{A_1-A_3}{A_1}F_{12} + \frac{A_3}{A_1}F_{13}\right]$$

where $A_1 = \pi\{(c_1)^2 - (c_2)^2 + (c_3)^2\}$: The area of ring and circle $A_2 = \pi(c_2)^2$: The area of inner ring $A_3 = \pi(c_3)^2$: The area of circle $F_{ij}$ may be represented as a matrix as follows:

$$\begin{Bmatrix}F_{11}\\F_{12}\\F_{13}\\F_{21}\\F_{22}\\F_{23}\\F_{31}\\F_{32}\\F_{33}\end{Bmatrix} = \begin{bmatrix}S_{11} & A_{11}\\S_{12} & A_{12}\\S_{13} & A_{13}\\S_{21} & A_{21}\\S_{22} & A_{22}\\S_{23} & A_{23}\\S_{31} & A_{31}\\S_{32} & A_{32}\\S_{33} & A_{33}\end{bmatrix}\begin{bmatrix}M_{S_0}\\M_{A_0}\end{bmatrix}$$

In these illustrative examples, i is the segment or segments of transducer 1400 acting as an actuator, and j is the segment or segments of transducer 1424 acting as a sensor. For example, i is 1 when segments 1402 and 1404 of transducer 1400 act as an actuator. When i is 2, segment 1402 acts an actuator, and when i is 3, segment 1404 acts as an actuator. When j is 1, segments 1406 and 1408 of transducer 1424 act as a sensor. When j is 2, segment 1406 acts as a sensor, and when j is 3, segment 1408 acts as a sensor.

In an advantageous embodiment, $S_{ij}$ and $A_{ij}$ are S0 and A0 mode scaling factors of signal $F_{ij}$. The zero-order symmetric and asymmetric modes $M_{S_0}$ and $M_{A_0}$ may be solved from the matrix equations by a controller, such as controller 340 in FIG. 3.

The controller identifies the pseudo-inverse of the scaling factor matrix. The controller then pre-multiplies the pseudo-inverse of the scaling factor matrix with the signal matrix. Once the pre-multiplication is performed, $M_{S_0}$ and $M_{A_0}$ may be calculated for the structure by multiplying the scaling factors $S_{ij}$ and $A_{ij}$ by the measured signal $F_{ij}$. $M_{S_0}$ and $M_{A_0}$ may be functions of voltage over time.

In an advantageous embodiment in which each $F_{ij}$ is a function of voltage over time, each $F_{ij}$ in the measured signal matrix may be presented as a line on a graph. For example, in FIGS. 15-20, illustrations of six graphs are depicted in accordance with an illustrative embodiment.

Figure 15:
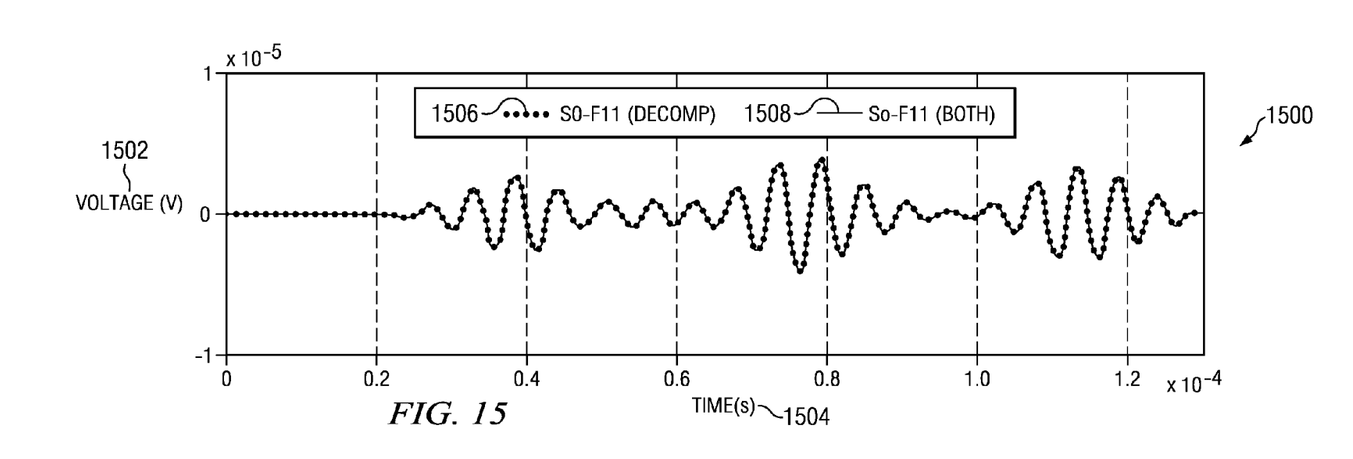
FIG. 15 is an illustration of a graph for the symmetric mode for the measured signal $F_{11}$ in accordance with an advantageous embodiment.

With reference first to FIG. 15, an illustration of a graph for the symmetric mode for the measured signal $F_{11}$ is depicted in accordance with an advantageous embodiment. Graph 1500 represents the symmetric mode for the measured signal when actuating with segments 1402 and 1404 and detecting waves with segment 1408 and segment 1406 from FIG. 14.

Graph 1500 comprises voltage axis 1502 and time axis 1504. Function 1506 represents the zero-order symmetric mode for $F_{11}$ as determined using the $F_{ij}$ signal matrix formed from measurements by transducer 1400 and transducer 1424. Function 1508 represents the zero-order symmetric mode for $F_{11}$ as determined using a two-sided measurement. That is, function 1508 was created by associating segment 308 with side 364 and segment 322 with side 366 in FIG. 3. In this advantageous embodiment, function 1506 is substantially the same as function 1508.

Figure 16:
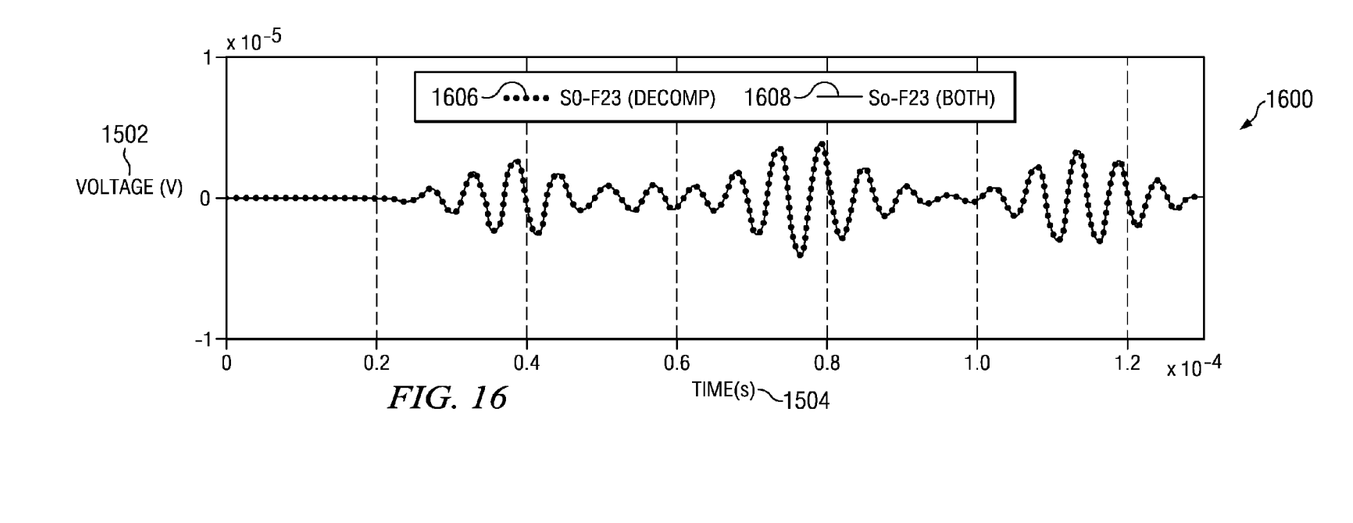
FIG. 16 is an illustration of a graph for the symmetric mode for the measured signal $F_{23}$ in accordance with an advantageous embodiment.

With reference next to FIG. 16, an illustration of a graph for the symmetric mode for the measured signal $F_{23}$ is depicted in accordance with an advantageous embodiment. Graph 1600 represents the symmetric mode for the measured signal when actuating with segment 1404 and the gap surrounding segment 1404 and detecting waves with segment 1408 from FIG. 14.

Function 1606 represents the zero-order symmetric mode for $F_{23}$ as determined using the $F_{ij}$ signal matrix formed from measurements by transducer 1400 and transducer 1424 in FIG. 14. Function 1608 represents the zero-order symmetric mode for $F_{23}$ as determined using a two-sided measurement. That is, function 1608 was created by associating segment 308 with side 364 and segment 322 with side 366 in FIG. 3. In this advantageous embodiment, function 1606 is substantially the same as function 1608.

Figures 17, 18:
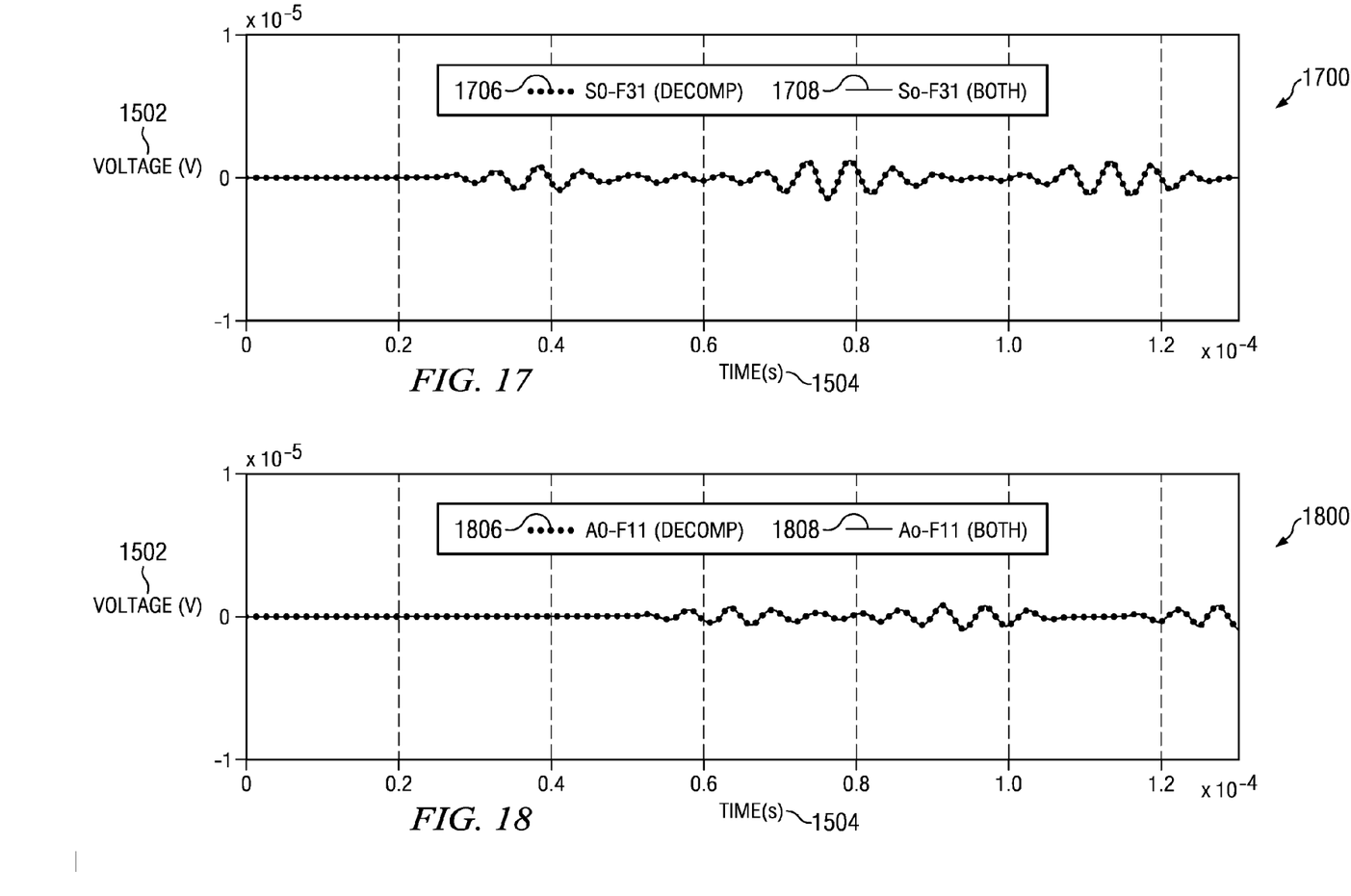
FIG. 17 is an illustration of a graph for the symmetric mode for the measured signal $F_{31}$ in accordance with an advantageous embodiment.
FIG. 18 is an illustration of a graph for the asymmetric mode for the measured signal $F_{11}$ in accordance with an advantageous embodiment.

Next, in FIG. 17, an illustration of a graph for the symmetric mode for the measured signal $F_{31}$ is depicted in accordance with an advantageous embodiment. Graph 1700 represents the symmetric mode for the measured signal when actuating with segment 1404 and detecting waves with segments 1406 and 1408 from FIG. 14.

Function 1706 represents the zero-order symmetric mode for $F_{31}$ as determined using the $F_{ij}$ signal matrix formed from measurements by transducer 1400 and transducer 1424 in FIG. 14. Function 1708 represents the zero-order symmetric mode for $F_{31}$ as determined using a two-sided measurement. That is, function 1708 was created by associating segment 308 with side 364 and segment 322 with side 366 in FIG. 3. In this advantageous embodiment, function 1706 is substantially the same as function 1708.

With reference to FIG. 18, an illustration of a graph for the asymmetric mode for the measured signal $F_{11}$ is depicted in accordance with an advantageous embodiment. Graph 1800 represents the asymmetric mode for the measured signal when actuating with segment 1402 and segment 1404 and detecting waves with segment 1406 and segment 1408 from FIG. 14.

Function 1806 represents the zero-order asymmetric mode for $F_{11}$ as determined using the $F_{ij}$ signal matrix formed from measurements by transducer 1400 and transducer 1424 in FIG. 14. Function 1808 represents the zero-order asymmetric mode for $F_{11}$ as determined using a two-sided measurement. That is, function 1808 was created by associating segment 308 with side 364 and segment 322 with side 366 in FIG. 3. In this advantageous embodiment, function 1806 is substantially the same as function 1808.

Figure 19:
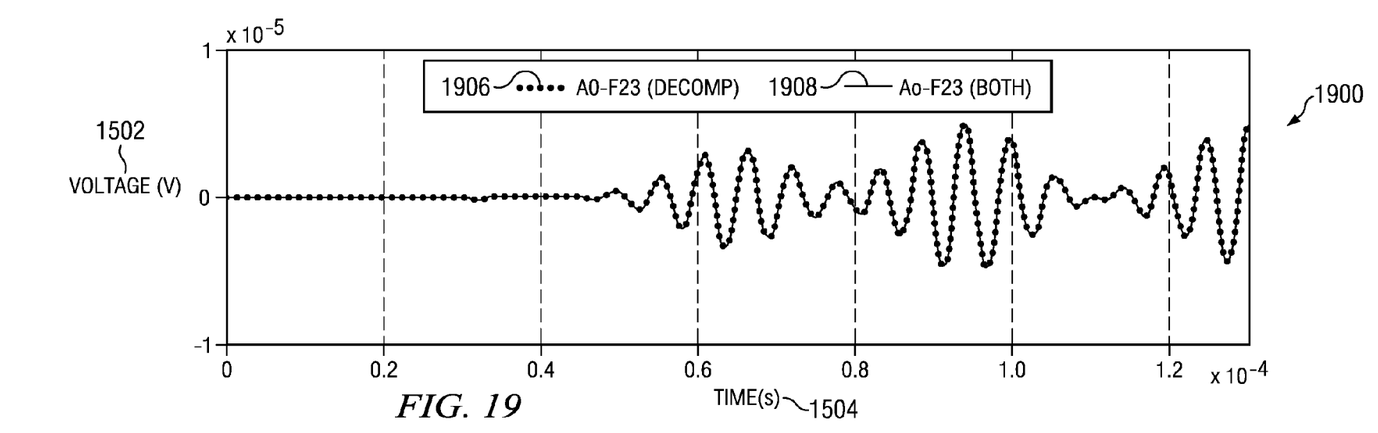
FIG. 19 is an illustration of a graph for the asymmetric mode for the measured signal $F_{23}$ in accordance with an advantageous embodiment.

With specificity to FIG. 19, an illustration of a graph for the asymmetric mode for the measured signal $F_{23}$ is depicted in accordance with an advantageous embodiment. Graph 1900 represents the asymmetric mode for the measured signal when actuating with segment 1404 and the gap surrounding segment 1404 and detecting waves with segment 1408 from FIG. 14.

Function 1906 represents the zero-order asymmetric mode for $F_{23}$ as determined using the $F_{ij}$ signal matrix formed from measurements by transducer 1400 and transducer 1424 in FIG. 4. Function 1908 represents the zero-order asymmetric mode for $F_{23}$ as determined using a two-sided measurement. That is, function 1908 was created by associating segment 308 with side 364 and segment 322 with side 366 in FIG. 3. In this advantageous embodiment, function 1906 is substantially the same as function 1908.

Figure 20:
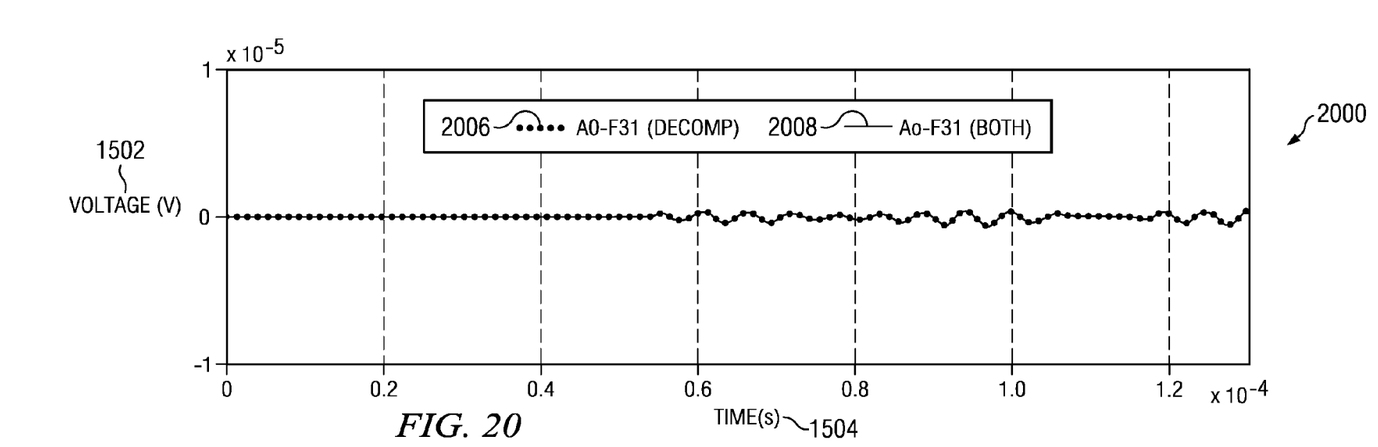
FIG. 20 is an illustration of a graph for the asymmetric mode for the measured signal $F_{31}$ in accordance with an advantageous embodiment.

With specificity to FIG. 20, an illustration of a graph for the asymmetric mode for the measured signal $F_{31}$ is depicted in accordance with an advantageous embodiment. Graph 2000 represents the asymmetric mode for the measured signal when actuating with segment 1404 and detecting waves with segments 1406 and 1408 from FIG. 14.

Function 2006 represents the zero-order asymmetric mode for $F_{31}$ as determined using the $F_{ij}$ signal matrix formed from measurements by transducer 1400 and transducer 1424 in FIG. 14. Function 2008 represents the zero-order asymmetric mode for $F_{31}$ as determined using a two-sided measurement. That is, function 2008 was created by associating segment 308 with side 364 and segment 322 with side 366 in FIG. 3. In this advantageous embodiment, function 2006 is substantially the same as function 2008.

Figure 21:
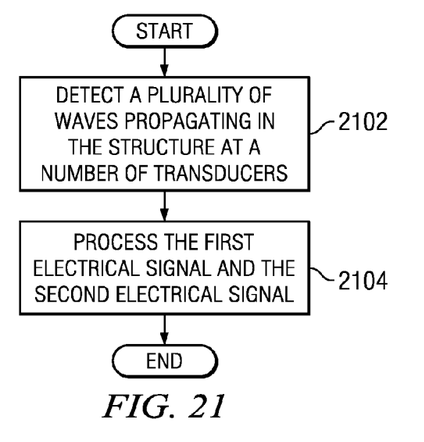
FIG. 21 is an illustration of a flowchart of a process for testing a structure in accordance with an advantageous embodiment.

Turning now to FIG. 21, an illustration of a flowchart of a process for testing a structure is depicted in accordance with an advantageous embodiment. The process may be performed in testing environment 300 by testing system 302 in FIG. 3.

The process begins by detecting a plurality of waves propagating in the structure at a number of transducers (operation 2102). Each transducer unit in the number of transducers may have a first segment and a second segment. The first and second segments are configured to generate a first electrical signal in response to detecting the plurality of waves propagating in the structure. The first segment and second segment are symmetric about two axes in a direction of wave propagation. The first and second segments have the same center.

The process then processes the first electrical signal and the second electrical signal (operation 2104). The processing may include using the first and second electrical signals to identify a mode or a number of modes within the waves. The process terminates thereafter.

Figure 22:
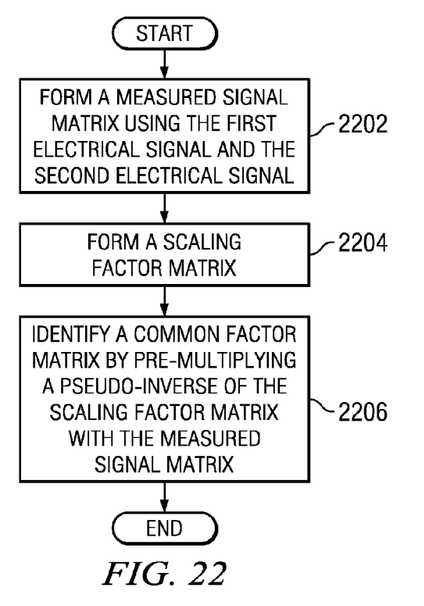
FIG. 22 is an illustration of a flowchart of a process for processing a first electrical signal and a second electrical signal in accordance with an advantageous embodiment.

Turning now to FIG. 22, an illustration of a flowchart of a process for processing a first electrical signal and a second electrical signal is depicted in accordance with an advantageous embodiment. The process may be performed in testing environment 300 by testing system 302 in FIG. 3. The process is an example implementation of operation 2104 in FIG. 21.

The process begins by forming a measured signal matrix using the first electrical signal and the second electrical signal (operation 2202). The measured signal matrix may represent the first electrical signal and the second electrical signal as functions of voltage over time.

The process then forms a scaling factor matrix (operation 2204). The scaling factor matrix contains a number of scaling factor values. The scaling factor values are real numbers. The scaling factor values are values that cause the number of modes sought in the test to equal the measured signal matrix.

The scaling factor matrix may be obtained using a second plurality of waves from a second test. In the second test, the transducers may be located farther apart than in the first test. The distance between the transducers is large enough that the number of modes may be identified. The distance is based on the properties of the structure.

The scaling factor matrix may also be obtained using any combination of a number of properties of the structure, a frequency of the plurality of waves, and dimensions of the first and second segments.

The process then identifies a common factor matrix by pre-multiplying a pseudo-inverse of the scaling factor matrix with the measured signal matrix (operation 2206). The common factor matrix comprises the number of modes from the plurality of modes. The number of modes indicates whether an inconsistency exists within the structure. A first mode in the number of modes may identify a particular inconsistency with greater accuracy than a second mode in the number of modes. Likewise, the second mode may identify a different inconsistency with greater accuracy than the first mode. The number of modes may comprise Lamb modes. The process terminates thereafter.

The process in FIG. 22 may obtain the scaling factor matrix prior to forming the measured signal matrix. The process in FIG. 22 may identify the structure and obtain the scaling factor matrix from a storage device in response to identifying the structure. The scaling factor matrix may be stored from a prior test or a baseline test.

Figure 23:
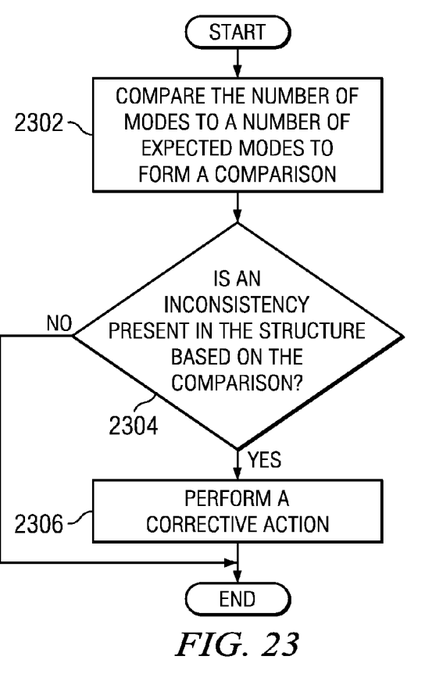
FIG. 23 is an illustration of a flowchart of a process for analyzing information obtained from a structure in accordance with an advantageous embodiment.

Turning now to FIG. 23, an illustration of a flowchart of a process for analyzing information obtained from a structure is depicted in accordance with an advantageous embodiment. The process may be performed in testing environment 300 by testing system 302 in FIG. 3. The process may be performed after operation 2206 in FIG. 22.

The process begins by comparing the number of modes to a number of expected modes to form a comparison (operation 2302). The number of expected modes may be identified using a measurement made in the past or using a model. In an advantageous embodiment, the number of expected modes is identified using a measurement made at a time it was believed there were no inconsistencies in the structure. In another advantageous embodiment, the measurement was made at a time there were no inconsistencies deemed unacceptable. In other words, an inconsistency may be present, but the inconsistency does not cause the structure to fall outside of a specification for the structure.

The number of expected modes may also be identified using a model. The model may generate the number of expected modes based on a number of properties of the structure, a frequency of the plurality of waves, and dimensions of the segments.

The process then determines whether an inconsistency is present in the structure based on the comparison (operation 2304). The process may determine that an inconsistency is present if the number of modes differs from the number of expected modes by a specified amount. If the process determines that the inconsistency is not present in the structure based on the comparison, the process terminates.

If the process determines that the inconsistency is present in the structure based on the comparison at operation 2304, the process performs a corrective action (operation 2306). The corrective action may be any combination of writing to a log, sending an alert, reworking the structure, and replacing the structure. The process terminates thereafter.

The flowcharts and block diagrams of the different depicted embodiments illustrate the architecture, functionality, and operation of some possible implementations of apparatus and methods in different advantageous embodiments. In this regard, each block in the flowcharts or block diagrams may represent a module, segment, function, and/or a portion of an operation or step. In some alternative implementations, the function or functions noted in the blocks may occur out of the order noted in the figures. For example, without limitation, in some cases, two blocks shown in succession may be executed substantially concurrently, or the blocks may sometimes be executed in the reverse order, depending upon the functionality involved. Also, other blocks may be added in addition to the illustrated blocks in the flowchart or block diagram.

The different advantageous embodiments provide increased productivity and greater accuracy of inconsistency determinations than achieved with prior art testing systems. Productivity and accuracy is increased by allowing a technician to test for multiple inconsistencies without making modifications to the transducers or the frequency of the waves.

Thus, the different advantageous embodiments provide a transducer unit, a testing system, and a method for testing a structure. The transducer unit comprises a first segment configured to generate a first electrical signal in response to detecting a plurality of waves propagating in a structure. The transducer unit also comprises a second segment configured to generate a second electrical signal in response to detecting the plurality of waves propagating in the structure.

The description of the different advantageous embodiments has been presented for purposes of illustration and description, and it is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A transducer unit comprising:
   a first segment configured to generate a first electrical signal in response to detecting a plurality of waves propagating in a structure; and
   a second segment configured to generate a second electrical signal in response to detecting the plurality of waves propagating in the structure, wherein the first segment and the second segment are selected from a group comprising an axial symmetric strip type, a concentric rectangular type, a concentric ring type, and a concentric circular and ring type.

2. The transducer unit of claim 1, wherein the first segment comprises a first electrode associated with a first piezoelectric material, and the second segment comprises a second electrode associated with a second piezoelectric material.

3. The transducer unit of claim 1 further comprising:
   the structure associated with the first segment and the second segment.

4. The transducer unit of claim 1 further comprising:
   a third segment configured to generate a third electrical signal in response to detecting the plurality of waves in the structure.

5. The transducer unit of claim 1, wherein the first segment has a center and is symmetric about two axes and the second segment has the center and is symmetric about the two axes.

6. The transducer unit of claim 5, wherein the first segment is symmetric about the two axes in a direction of wave propagation and the second segment is symmetric about the two axes in the direction of the wave propagation.

7. A testing system comprising:
a number of transducers in which each transducer unit in the number of transducers comprises a first segment configured to generate a first electrical signal in response to detecting a plurality of waves propagating in a structure and a second segment configured to generate a second electrical signal in response to detecting the plurality of waves propagating in the structure, wherein the first segment has a center and is symmetric about two axes in a direction of wave propagation, and the second segment has the center and is symmetric about the two axes in the direction of the wave propagation; and
a controller configured to receive the first electrical signal and the second electrical signal and process the first electrical signal and the second electrical signal, wherein in processing the first electrical signal and the second electrical signal, the controller is configured to construct a measured signal matrix using the first electrical signal and the second electrical signal, create a scaling factor matrix, and form a common factor matrix using the measured signal matrix and the scaling factor matrix.

8. The testing system of claim 7, wherein the controller being configured to process the first electrical signal and the second electrical signal further comprises the controller being configured to process the first electrical signal and the second electrical signal to identify a number of modes within a plurality of modes in the plurality of waves.

9. The testing system of claim 8, wherein the number of modes is a number of Lamb modes.

10. The testing system of claim 7, wherein in processing the first electrical signal and the second electrical signal, the controller is configured to process the first electrical signal and the second electrical signal to identify a mode within a plurality of modes in the plurality of waves propagating in the structure.

11. The testing system of claim 7, wherein the first segment comprises a first electrode associated with a first piezoelectric material and the second segment comprises a second electrode associated with a second piezoelectric material.

12. The testing system of claim 7 further comprising:
the structure associated with the first segment and the second segment.

13. The testing system of claim 7 further comprising:
a third segment configured to generate a third electrical signal in response to detecting the plurality of waves propagating in the structure.

14. The testing system of claim 7, wherein the first segment has a center and is symmetric about the two axes, and the second segment has the center and is symmetric about the two axes.

15. The testing system of claim 14, wherein the first segment has the center and is symmetric about the two axes in the direction of the wave propagation, and the second segment has the center and is symmetric about the two axes in the direction of the wave propagation.

16. The testing system of claim 7, wherein the first segment and the second segment are selected from a group comprising an axial symmetric strip type, a concentric rectangular type, a concentric ring type, and a concentric circular and ring type.

17. The testing system of claim 7, wherein the number of transducers are associated with the structure.

18. A method for testing a structure, the method comprising:
detecting a plurality of waves propagating in the structure at a number of transducers, each transducer unit in the number of transducers comprising a first segment configured to generate a first electrical signal in response to detecting the plurality of waves and a second segment configured to generate a second electrical signal in response to detecting the plurality of waves propagating in the structure, wherein the first segment has a center and is symmetric about two axes in a direction of wave propagation, and the second segment has the center and is symmetric about the two axes in the direction of the wave propagation;
forming a measured signal matrix using the first electrical signal and the second electrical signal; and
forming a scaling factor matrix, wherein the scaling factor matrix comprises a number of scaling factor values.

19. The method of claim 18, wherein the plurality of waves is a first plurality of waves, wherein the first plurality of waves is propagated in the structure when the number of transducers is a first distance apart, wherein the number of scaling factor values is obtained using a second plurality of waves, and wherein the second plurality of waves is detected when the number of transducers is at a second distance apart.

20. The method of claim 18, wherein the structure comprises a first side and a second side, wherein the plurality of waves is a first plurality of waves, wherein the first plurality of waves is propagated in the structure when the number of transducers are associated with the first side, wherein the number of scaling factor values is obtained using a second plurality of waves, and wherein the second plurality of waves is detected when the number of transducers is associated with the first side and the second side.

21. The method of claim 18, wherein the number of scaling factor values is simulated using a number of properties of the structure, a frequency of the plurality of waves, dimensions of the first segment, and dimensions of the second segment.

22. The method of claim 18, wherein the step of processing the first electrical signal and the second electrical signal to form the result further comprises:
identifying a common factor matrix by pre-multiplying a pseudo-inverse of the scaling factor matrix with the measured signal matrix.

23. The method of claim 22, wherein the plurality of waves comprises a plurality of modes, and wherein the common factor matrix comprises a number of modes in the plurality of modes.

24. The method of claim 23, wherein the number of modes is a mode.

25. The method of claim 24, wherein the mode is a number of Lamb modes.

26. The method of claim 24, wherein the mode is selected from a group of a symmetric mode and an asymmetric mode.

27. The method of claim 23 further comprising:
comparing the number of modes to a number of expected modes to form a comparison;
determining whether an inconsistency is present in the structure based on the comparison;
responsive to determining that the inconsistency is present in the structure, performing a corrective action.

* * * * *